Figure 1:
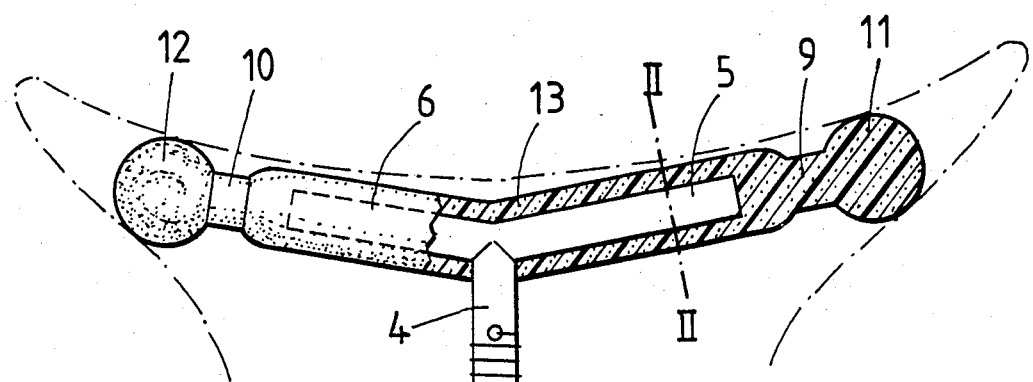

United States Patent [19]

Cimber

[11] Patent Number: 4,628,924

[45] Date of Patent: Dec. 16, 1986

[54] INTRAUTERINE CONTRACEPTIVE DEVICE

[76] Inventor: Hugo Cimber, Neufeldstrasse 134, 3012 Bern, Switzerland

[21] Appl. No.: 571,570

[22] Filed: Jan. 17, 1984

[30] Foreign Application Priority Data

Jan. 20, 1983 [CH] Switzerland ............... 323/83

[51] Int. Cl.⁴ ............................................. A61F 5/46
[52] U.S. Cl. ........................................... 128/130
[58] Field of Search ................................ 128/130

[56] References Cited

U.S. PATENT DOCUMENTS

| | | | |
|---|---|---|---|
| 3,405,711 | 10/1968 | Bakunin | 128/130 |
| 3,628,530 | 12/1971 | Schwartz | 128/130 |
| 3,656,483 | 4/1972 | Rudel | 128/130 |
| 3,678,927 | 7/1972 | Soichet | 128/130 |
| 3,842,826 | 10/1974 | Nolan | 128/130 |
| 3,918,443 | 11/1975 | Vennard et al. | 128/130 |
| 3,923,051 | 12/1975 | Soichet | 128/130 |
| 3,994,291 | 11/1976 | Salmagian | 128/130 |
| 4,034,749 | 7/1977 | Von Kesserü et al. | 128/130 |
| 4,038,978 | 8/1977 | Morris et al. | 128/130 |
| 4,509,504 | 4/1985 | Brundin | 128/130 |
| 4,537,186 | 8/1985 | Verschoof et al. | 128/130 |

*Primary Examiner*—Robert Peshock
*Assistant Examiner*—C. W. Shedd
*Attorney, Agent, or Firm*—Ronald G. Goebel

[57] ABSTRACT

The device, intended for insertion by means of a tube, comprises a supporting part having two branches attached to the front end in such a way that they spring apart when the device is pushed out of the tube into the uterus. At the end of each branch is a spherical occluding member, and at the rearward end of the supporting part is an eye through which a thread is looped. In order to achieve gentle sealing solely of the mouths of the Fallopian tubes, as well as to reduce production costs, the occluding members are of soft material and are flexibly connected to the associated branches, while the supporting part and the branches are made in one piece of a resilient but comparatively stiff material.

2 Claims, 3 Drawing Figures

INTRAUTERINE CONTRACEPTIVE DEVICE

This invention relates to contraceptive devices, and more particularly to an intrauterine contraceptive device of the type to be introduced into the uterus by means of a small tube and having a supporting part with two branches attached to the forward end thereof, considered in the direction of insertion, in such a way that after their ejection from the tube they spread away from one another laterally.

Intrauterine contraceptive devices (IUDs) in the form of rigid one-piece or multipart bodies are known. They are troublesome to insert and remove, and they do not exclude the risk of injury to the mucous membrane or of burrowing into the uterine wall.

Particularly in order to avoid these disadvantages to a certain extent, IUDs have also been proposed with arms which spring away from each other, each arm being provided with an end body whose curved outside surface serves to reduce the risk of injury to the mucous membrane somewhat, as well as to form an ovoid when folded together. Such end bodies, however, are naturally neither intended nor suited to exercise any sort of sealing function. These IUDs, which are, moreover, often wound with copper wire as well, possess a certain contraceptive effect attributable to irritation of the mucous membrane by the foreign body thus introduced.

Finally, IUDs have been proposed which comprise occluding members inflatable by means of an appropriate feed line. Depending upon the design of such IUDs having inflatable occluding members, the latter can be very effective because if, for example, the occluding members take the form of inflatable spherical bodies having very thin walls, they make it possible to seal the mouths of the Fallopian tubes tightly without irritating the uterine mucous membrane or burrowing into it since, owing to the described construction, they can be made very soft. Furthermore, such IUDs allow menstrual blood to flow out freely. As advantageous as these IUDs might be, however, their manufacture poses a great many problems; if it is feasible at all, the resultant IUDs are so expensive that they cannot come into widespread use. Another drawback of IUDs made solely of soft, inflatable material is that they may not absolutely perform the task of sealing the mouths of the Fallopian tubes opening into the uterus since in most cases they do not spread apart as desired.

It is an object of this invention to provide an improved intrauterine contraceptive device which, owing to the soft part thereof, does not cause any irritation of the uterine mucous membrane or wall, but owing to the rigid part, can be properly positioned in the uterus in order to seal the mouths of the Fallopian tubes securely without hindering the flow of menstrual blood, and which is also comparatively simple to manufacture.

To this end, in the intrauterine contraceptive device according to the present invention, of the type initially mentioned, the improvement comprises branches bearing at their free ends spherical occluding members which are intended and suited solely to seal the mouths of the Fallopian tubes in the uterus, the occluding members being made of soft material and being connected in a flexible manner to the respective branch ends, while the supporting part and the branches are made in one piece and of a resilient but comparatively stiff material.

Figure 2:
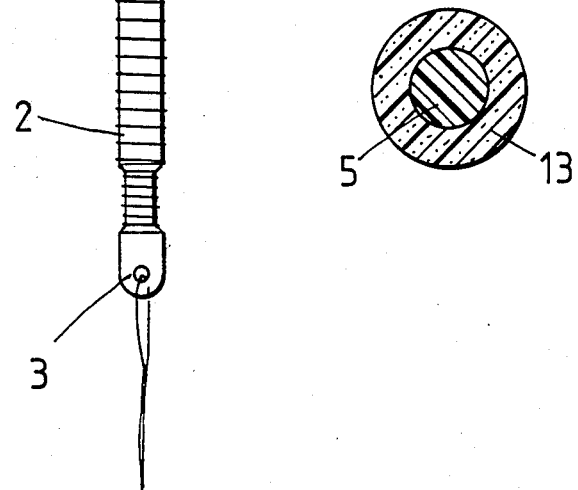
Figure 3:
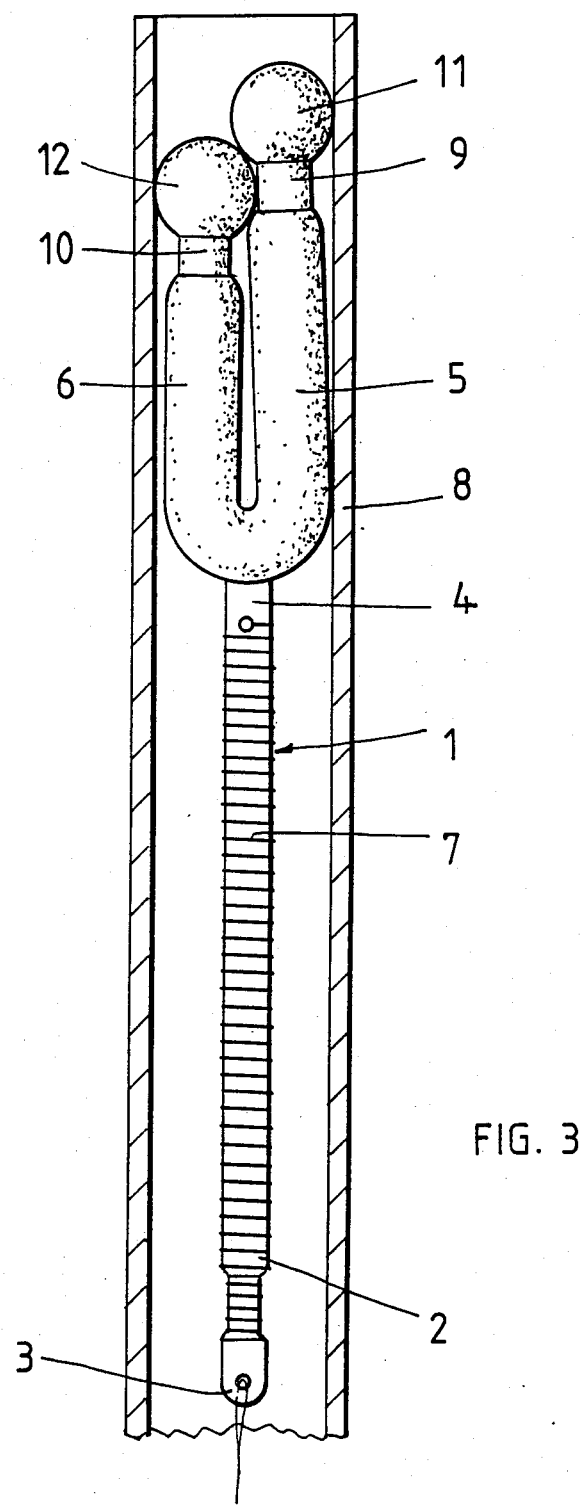

A preferred embodiment of the invention will now be described in detail with reference to the accompanying drawings, in which:

FIG. 1 is a view of the IUD partly in elevation and partly in section, the uterus being indicated by a dot-dash line, FIG. 2 is a section taken on the line II—II of FIG. 1, and FIG. 3 is a section through the insertion tube, showing the position of the two branches when the IUD is pulled into the tube.

In the embodiment illustrated, the IUD comprises a supporting part 1, the rearward end 2 of which, relative to the direction of insertion, includes an eye 3 through which an extraction thread is looped, whereas at the other, front end 4 of part 1, two branches 5 and 6 made of the same material as part 1 are disposed. As shown in FIG. 1, part 1 may be wound with a filament 7 of copper, the contraceptive properties of which are generally known. The material of which part 1 and branches 5 and 6 are made is a comparatively stiff but largely resilient plastic. Thus, when the IUD is inserted in a tube 8, for example, as is shown in FIG. 3, and is then pushed from the illustrated position toward the front (upward as viewed in the drawing) until the junction point of the two branches 5 and 6, which are of different lengths, exits from the upper end of tube 8, branches 5 and 6 spread apart from one another laterally into the position shown in FIG. 1.

Branches 5 and 6 are covered with an extremely soft, elastic material, such as silicone rubber (e.g., the product sold under the registered trademark "SILASTIC 382" by Dow Corning). As a continuation of the free ends of branches 5 and 6, this covering 13 merges into connecting parts 9 and 10 of smaller diameter, provided for increasing flexibility, adjacent to which substantially spherical occluding members 11 and 12 made of the same soft material are respectively disposed.

With the IUD in the position shown in FIG. 3, it is introduced into the uterus by means of tube 8, after which it is pushed out of tube 8 at the front by a rod or other suitable means. It will be seen from the position of the IUD when folded up within insertion tube 8 that because of the differing lengths of branches 5 and 6, spherical occluding member 12 of branch 6 rests against connecting part 9 of branch 5, whereby the diameter of the IUD as a whole is considerably reduced. As a result of this, and also of the fact that occluding members 11 and 12 are of extremely soft material, both introduction and extraction of the IUD can take place painlessly.

As soon as the IUD is pushed sufficiently far out of tube 8, branches 5 and 6 spread apart owing to the stiffness of their material and assume the position shown in FIG. 1, in which occluding members 11 and 12 lie gently and smoothly against the uterine mucous membrane at the mouths of the Fallopian tubes and thereby seal the latter tightly. Owing to the softness of the material of which occluding members 11 and 12 are made, as well as to connecting parts 9 and 10, members 11 and 12 can adapt to the particular characteristics of the uterus; and the part of the IUD extending beyond the comparatively stiff end of each branch 5 or 6 and consisting of a connecting part 9 or 10 and an occluding member 11 or 12 is capable of effecting the desired seal, even being deformed for this purpose, if need be.

The IUD is removed from the body in the usual manner by means of the thread looped through eye 3. When this thread is pulled, supporting part 1 and branches 5 and 6, which can be folded up with elastic deformation, are brought into the position illustrated in FIG. 3 thanks to the differing lengths of branches 5 and 6, and the IUD can thus be drawn out through the cervix.

The IUD described above ensures that the mouths of the Fallopian tubes are securely sealed in the most gentle manner, i.e., avoiding any irritation of the uterine mucous membrane and allowing menstrual blood to flow out freely. It can be painlessly introduced and just as painlessly taken out. Moreover, its manufacture poses no particular problems, so that this IUD is suitable for widespread use.

What is claimed is:

1. An intrauterine contraceptive device of the type intended to be introduced into the uterus by means of a tube, having a supporting part with a proximal and a distal end, and having two branches joined to the proximal end of said supporting part in such a way that said branches spread apart from one another laterally upon ejection from said tube, wherein the improvement comprises;
    (a) a substantially spherical occluding member made of a soft material and flexibly connected to the end of each of said branches remote from the point of junction thereof with said proximal end of said supporting part, said supporting part and said branches being made in one piece of a comparatively stiff but resilient material; and
    (b) a connecting piece made of easily deformable, soft material and disposed between each said occluding member and the respective end of the associated one of said branches.

2. An intrauterine contraceptive device of the type intended to be introduced into the uterus by means of a tube, having a supporting part with a proximal and a distal end, and having two branches joined to the proximal end of said supporting part in such a way that said branches spread apart from one another laterally upon ejection from said tube, wherein the improvement comprises;
    (a) a substantially spherical occluding member made of a soft material and flexibly connected to the end of each of said branches remote from the point of junction thereof with said proximal end of said supporting part, said supporting part and said branches being made in one piece of a comparatively stiff but resilient material, said branches being covered with said soft material; and
    (b) a connecting piece made of easily deformable, soft material and disposed between each said occluding member and the respective end of the associated one of said branches.

* * * * *